United States Patent

Ramsay et al.

[11] Patent Number: 5,973,205
[45] Date of Patent: Oct. 26, 1999

[54] PROCESS FOR THE PREPARATION OF 1, 3-DIAMINOPROPANE DERIVATIVES AND INTERMEDIATES USEFUL IN THIS PROCESS

[75] Inventors: Thomas Weir Ramsay, Suffolk; Robin Patrick Attrill, Essex, both of United Kingdom

[73] Assignee: SmithKline Beecham plc, Brentford, United Kingdom

[21] Appl. No.: 08/981,812

[22] PCT Filed: Jul. 8, 1996

[86] PCT No.: PCT/EP96/02998

§ 371 Date: Apr. 23, 1998

§ 102(e) Date: Apr. 23, 1998

[87] PCT Pub. No.: WO97/02231

PCT Pub. Date: Jan. 23, 1997

[30] Foreign Application Priority Data

Jul. 6, 1995 [GB] United Kingdom .................... 9513756

[51] Int. Cl.$^6$ .................................................. C07C 209/00
[52] U.S. Cl. ........................ 564/367; 564/336; 564/372; 564/373; 564/374; 564/397
[58] Field of Search ..................... 564/336, 367, 564/372, 373, 374, 397

[56] References Cited

U.S. PATENT DOCUMENTS 3,707,563  12/1972  Piki .
5,442,120   8/1995  Van Der Meji .................... 564/375
5,494,933   2/1996  Maschler ............................ 514/619

FOREIGN PATENT DOCUMENTS 0 233 762 A2  2/1987  European Pat. Off. .
0 614 905     9/1994  European Pat. Off. .

OTHER PUBLICATIONS

Chesney, et al., Synth. Commun; vol. 20, No. 20; 1990, pp. 3167–3180.
Boor, et al., Chemical Abstracts; vol. 112, No. 17; 1990, Abstract No. 153201.
Oki, et al., Chemical Abstracts; vol. 70, No. 5; 1969, Abstract No. 18601.

Primary Examiner—Gary Geist
Assistant Examiner—Jean F Vollano
Attorney, Agent, or Firm—Mary E. McCarthy; Stephen Venetianer; Charles M. Kinzig

[57] ABSTRACT

A process for preparing a compound of formula (I) or an addition salt thereof and/or a solvate thereof:

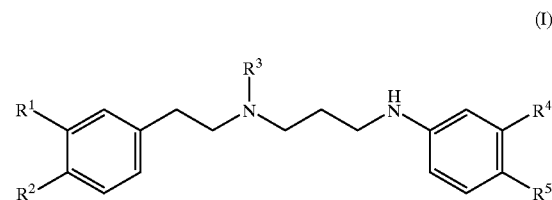

(I)

wherein $R^1$, $R^2$, $R^4$ and $R^5$ are each independently $C_{1-4}$ alkoxy and $R^3$ is $C_{1-6}$ alkyl, which process comprises reacting an arylamine of formula (II):

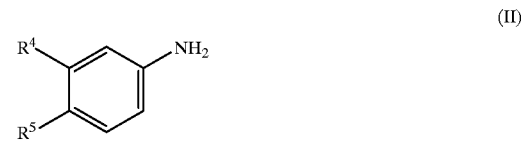

(II)

wherein $R^4$ and $R^5$ are as defined in relation to formula (I) with a β-aminoaldehyde of formula (III):

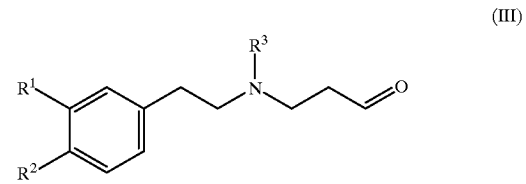

(III)

wherein $R^1$, $R^2$ and $R^3$ are as defined in relation to formula (I); and thereafter reducing the intermediate so formed and, optionally, forming an addition salt of the compound of formula (I) and/or a solvate thereof.

7 Claims, No Drawings

PROCESS FOR THE PREPARATION OF 1,3-DIAMINOPROPANE DERIVATIVES AND INTERMEDIATES USEFUL IN THIS PROCESS

This application is the national phase of PCT/EP96/02998 filed Jul. 8, 1996.

This invention relates to a novel process, to certain novel compounds prepared by such process, to pharmaceutical compositions comprising such compounds and to the use of such compounds in medicine.

European Patent Application, Publication Number 233762 discloses certain compounds of formula (A):

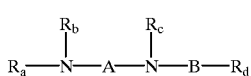

(A)

wherein $R_a$ and $R_d$ are independently phenyl optionally substituted by one, two or three of halogen, trifluoromethyl, $C_{1-4}$ alkoxy, $C_{1-4}$ alkyl, cyano, hydroxy, nitro, $NR_eR_f$ or $O_2SNR_eR_f$ wherein $R_e$ and $R_f$ are independently hydrogen or $C_{1-6}$ alkyl or together are $C_{3-6}$ polymethylene, or disubstituted at adjacent carbon atoms by $C_{1-2}$ alkylenedioxy and optionally further substituted by one of the above groups;

$R_b$ is selected from $(CH_2)_z$ CN where z is 0 or an integer from 1 to 4, $C_{1-12}$ alkyl $C_{3-7}$ cycloalkyl, $C_{3-7}$ cycloalkyl $C_{1-4}$ alkyl, phenyl $C_{1-4}$ alkyl, pyridyl, pyridyl $C_{1-4}$ alkyl, $COR_g$, $COCH_2COR_g$, $SO_2R_g$, $CO_2R_g$, $CONHR_g$ and $CSNHR_g$, where $R_g$ is selected from $C_{3-12}$ alkyl, $C_{3-7}$ cycloalkyl, $C_{3-7}$ cycloalkyl $C_{1-4}$ alkyl, phenyl and phenyl $C_{1-4}$ alkyl, any alkyl moiety in $R_g$ optionally substituted by hydroxy or $C_{1-4}$ alkanoyloxy, any pyridyl or phenyl moiety in $R_b$ optionally substituted as defined for $R_a$ and $R_d$ and any cycloalkyl moiety in $R_b$ optionally substituted by one or two $C_{1-4}$ alkyl groups;

$R_c$ is hydrogen or $C_{1-4}$ alkyl;

A represents $C_{2-5}$ alkylene; and

B represents $C_{1-4}$ alkylene; which compounds are stated to possess cardiovascular activity, in particular anti-angina activity.

EP233762 also discloses intermediates for the preparation of the compound of formula (A) of formula (B):

(B)

in which $R_a$, $R_c$, $R_d$, A, and B are as defined with respect to formula (A) or are groups convertible thereto.

One particular compound from EP 233762 is the compound of Example 50 which is N-(3,4-dimethoxyphenyl)-N-[3-[[2-(3,4dimethoxyphenyl)ethyl]methylamino]propyl]-4-nitrobenzamide hydrochloride (hereinafter Compound I).

EP233762 discloses a range of alternative methods of preparing the compound of formula (B).

Synthetic Communications 20, 3167–3180, (1990) discloses the preparation of β-aminoaldehydes. These compounds are stated to be unstable but they are demonstrated to react in situ with a range of different reagents to provide various aminated products.

We have now found that in addition to the reagents disclosed in Synthetic Communications, a β-aminoaldehyde reacts with certain arylamines to provide arylimines which are readily reduced to a compound of formula (B) wherein variable A represents $C_3$ alkylene. The reactions are high yielding and are readily carried out in the same reaction vessel providing a useful 'one pot' synthesis of the intermediate compounds (B) wherein variable A represents $C_3$ alkylene and in particular the intermediate to Compound I.

Accordingly, in its most preferred aspect the present invention provides a process for preparing a compound of formula (I) or an addition salt thereof and/or a solvate thereof:

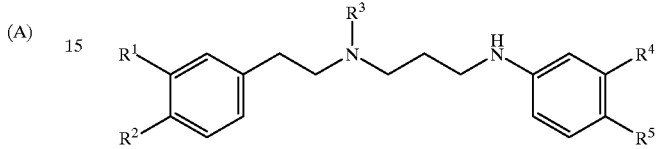

(I)

wherein $R^1$, $R^2$, $R^4$ and $R^5$ are each independently $C_{1-4}$ alkoxy and $R^3$ is $C_{1-6}$ alkyl, which process comprises reacting an arylamine of formula (II):

(II)

wherein $R^4$ and $R^5$ are as defined in relation to formula (I) with a β-aminoaldehyde of formula (III):

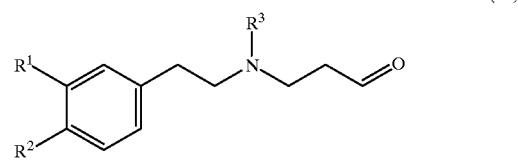

(III)

wherein $R^1$, $R^2$ and $R^3$ are as defined in relation to formula (I); and thereafter reducing the intermediate so formed and, optionally, forming an addition salt of the compound of formula (I) and/or a solvate thereof.

Generally, the intermediate is an imine. The reaction is suitably carried out in an aprotic solvent, preferably tetrahydrofuran at any temperature providing a suitable rate of formation of the final product including temperatures up to room temperature, but usually at a temperature below room temperature such as a temperature in the range of –15° C. to 10° C., for example at 0° C.

A compound of formula (III) may be prepared by the conjugate addition of acrolein to an amine of formula (IV):

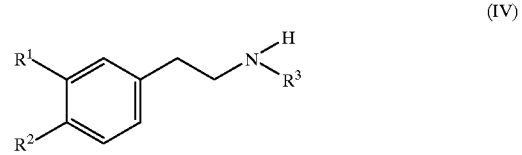

(IV)

wherein $R^1$, $R^2$ and $R^3$ are as defined in relation to the compounds of formula (I).

The reaction is suitably carried out in an aprotic solvent, preferably tetrahydrofuran at any temperature providing a suitable rate of formulation of the final product including temperatures such as room temperature, but usually at a temperature below room temperature, such as a temperature in the range of −15° C. to 5° C.

Preferably, $R^1$, $R^2$, $R^4$ and $R^5$ each independently represent methoxy. Preferably, $R^3$ represents methyl.

As indicated above, the reaction between the compounds of formulae (II) and (III) proceeds via an intermediate, generally an imine, which is subsequently reduced to the compound of formula (I).

In a further aspect, the invention provides a process for preparing a compound of the above defined formula (I), or an addition salt thereof and/or a solvate thereof which comprises reducing an intermediate compound prepared, and suitably isolated, from the reaction between a compound of formula (II) and a compound of formula (III) and, optionally, forming an addition salt of the compound of formula (I) and/or a solvate thereof.

In a particular aspect the present invention provides a process for preparing a compound of the above defined formula (I), or an addition salt thereof and/or a solvate thereof, which comprises reducing a compound of formula (V):

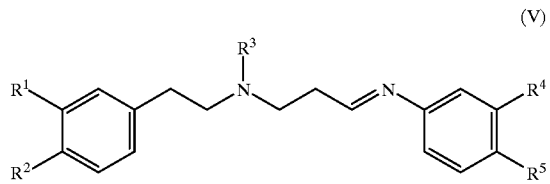

(V)

wherein $R^1$, $R^2$, $R^4$ and $R^5$ are each independently $C_{1-4}$ alkoxy and $R^3$ is $C_{1-6}$ alkyl and, optionally, forming an addition salt of the compound of formula (I) and/or a solvate thereof.

The above mentioned reductions may be carried out using any suitable reducing procedure including catalytic hydrogenation, using catalysts such as palladium on carbon, for example 10% palladium on carbon, and metal hydride reduction, using such reagents as sodium borohydride.

Catalytic hydrogenation is usually the preferred reduction method.

The reaction conditions for the reduction are those conditions conventionally used for the particular reduction method chosen. For example when 10% palladium on carbon is used the reaction is carried out in tetrahydrofuran at below 30° C., usually at a elevated pressure, such as 40–50 psi, although the reaction will proceed at lower pressures such as atmosphere pressure.

As indicated above the compound of formula (I) may be converted into an acid addition salt. A further aspect of the invention is a process for the preparation of an acid addition salt of a compound of the above defined formula (I), which process comprises treating the compound of formula (I) with an appropriate source of an acid.

A preferred source of an acid is hydrogen chloride.

The amount of acid used in the reaction can affect the quality of the final product For example when hydrogen chloride is used the amount of acid added is the stoichiometric amount required by the calculated yield of free base.

In its most preferred aspect the present invention provides a process for preparing a compound of formula (I), or an acid addition salt thereof, which involves the following steps being carried out without isolating intermediate compounds (III) and/or (V):

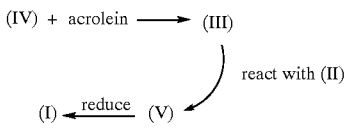

and optionally thereafter forming an acid addition salt of the compound of formula (I).

Suitable reaction conditions are as described in relation to the reaction between the compounds of formulae (II) and (III).

Preferably, the reaction between a compound of formula (IV) and acrolein is carried out in the presence of a catalytic amount of 1,8-diazobicyclo[5.4.0]undec-7-ene (DBU).

The compounds of formula (II) may be prepared according to known methods, for example by use of the methods disclosed in S. P. Findlay & G. Dougherty, J. Org. Chem. (1948) 13 560.

The compounds of formula (IV) may be prepared according to known methods, for example by use of the methods disclosed in Paul Anand, J. Scient., Ind. Res India 17B (1958) 219, 223

As stated above the present process is suitable for the preparation of compounds of formula (B) wherein variable A represents $C_3$ alkylene.

Accordingly in a further aspect the present invention provides a process for the preparation of a compound of the above defined formula (B) in which variable A represents $C_3$ alkylene, or an addition salt and/or a solvate thereof, which process comprises reacting a compound of formula (VI):

$$R_a\text{—}NH_2 \quad \quad (VI)$$

wherein
$R_a$ represents phenyl optionally substituted by one, two or three of halogen, trifluoromethyl, $C_{1-4}$ alkoxy, $C_{1-4}$ alkyl, cyano, hydroxy, nitro, $NR_eR_f$ or $O_2SNR_eR_f$ wherein $R_e$ and $R_f$ are independently hydrogen or $C_{1-6}$ alkyl or together are $C_{3-6}$ polymethylene, or disubstituted at adjacent carbon atoms by $C_{1-2}$ alkylenedioxy and optionally further substituted by one of the above groups; with a compound of formula (VII):

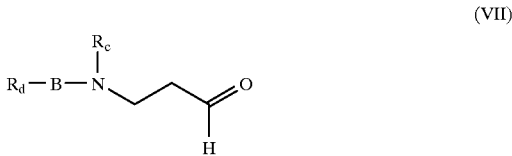

(VII)

wherein, $R_d$ represents phenyl optionally substituted by one, two or three of halogen, trifluoromethyl, $C_{1-4}$ alkoxy, $C_{1-4}$ alkyl, cyano, hydroxy, nitro, $NR_eR_f$ or $O_2SNR_eR_f$ wherein $R_e$ and $R_f$ are independently hydrogen or $C_{1-6}$ alkyl or together are $C_{3-6}$ polymethylene, or disubstituted at adjacent carbon atoms by $C_{1-2}$ alkylenedioxy and optionally further substituted by one of the above groups;
$R_c$ is hydrogen or $C_{1-4}$ alkyl; and
B represents $C_{1-4}$ alkylene; and thereafter reducing the intermediate so formed and, optionally, forming an addition salt of the compound of formula (B) and/or a solvate thereof.

Generally, the intermediate is an imine.

The reaction conditions for the reaction between the compounds of formulae (VI) and (VII) are analogous to those used in the reaction between the compounds of formulae (II) and (III).

A compound of formula (VI) may be prepared in an analogous manner to that described for the compound of formula (II).

A compound of formula (VII) may be prepared in an analogous manner to that described for the compound of formula (III).

The preferred forms of the reaction between the compounds of formulae (VI) and (VII) to give the compound of formula (B), are as described for the reactions between the compounds of formulae (II) and (III), including the isolation and reduction of an intermediate analogous to the imine of formula (V) discribed above.

The compounds of formulae (III), (V) and (VII) also form part of the present invention, especially for use as intermediates.

The following Example illustrates the invention but does not limit it in any way.

Preparation of N-[2-(3,4-Dimethoxyphenyl)ethyl]-N-methyl-N'-(3,4-dimethoxyphenyl)-1,3-propanediamine, hydrochloride with 4.74 molar hydrogen chloride in ethanol (303 ml). The solution was stirred for 1 hour then cooled at ca. 0° C. for ca. 1.5 hours. The resulting suspension was filtered, washed with tetrahydrofuran and air dried to give N-[2-(3,4-Dimethoxyphenyl)ethyl]-N-methyl-N'-(3,4-dimethoxyphenyl)-1,3-propanediamine hydrochloride as an off white solid, 557 g.

A sample of the crude product (180 g) was recrystallised from ethanol (1050 ml) to give the product as an off white solid, 170 g (60% overall yield).

δ(DMSO): 1.95–2.02 (m, 2H); 2.77 (s, 3H); 2.97–3.01 (m, 2H); 3.07 (t, J=6.5 Hz, 2H); 3.17–3.25 (m, 4H); 3.36 (bs, 1H) 3.62 (s, 3H); 3.70 (s, 3H); 3.72 (s, 3H); 3.75 (s, 3H); 6.08 (dd, J=2.5, 8.5 Hz, 1H); 6.31 (d, J=2.5 Hz, 1H); 6.72 (d, J=8.5 Hz, 1H); 6.77 (dd, J=1.8, 8.2 Hz, 1H); 6.87–6.91 (m, 2H)

We claim:

1. A process for preparing a compound of formula (I) or an addition salt thereof and/or a solvate thereof:

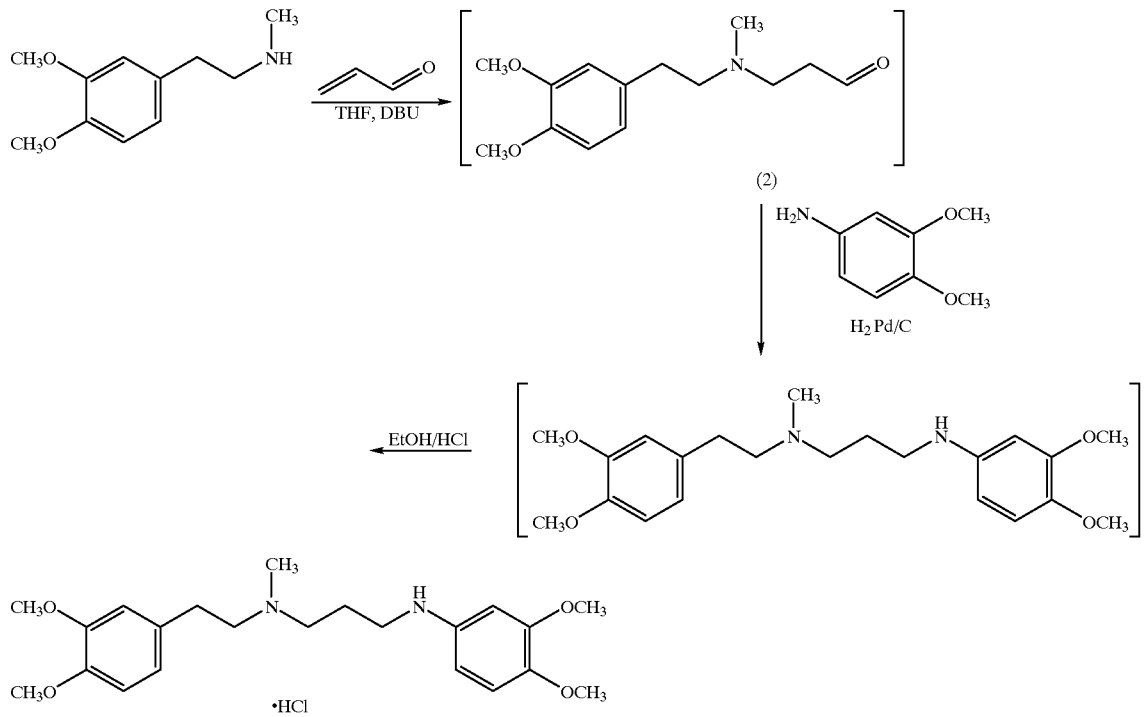

Tetrahydrofuran (2.5 L) was cooled to ca. 0° C. under a nitrogen atmosphere and 90% acrolein (152 ml) was added. A solution of 3,4-dimethoxy-N-methylphenethylamine (400 g) and DBU (3.2 ml) in tetrahydrofuran (1 L) was then added slowly with stirring and cooling over 23 mins maintaining the temperature below 5° C. A further amount of tetrahydrofuran (250 ml) was used to wash in any remaining solution in the addition funnel. The reaction mixture was stirred for 30 mins at ca. 0° C then added to 3,4-dimethoxyaniline (315 g) and 10% palladium on carbon (40 g). The mixture was then hydrogenated at ambient temperature, 40–50 psi. pressure for ca 20 hours. The catalyst was removed by filtration and the filtrate treated wherein $R^1$, $R^2$, $R^4$ and $R^5$ are each independently $C_{1-4}$ alkoxy and $R^3$ is $C_{1-6}$ alkyl,
which process comprises reacting an arylamine of formula (II):

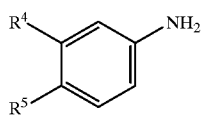

wherein $R^4$ and $R^5$ are as defined in relation to formula (I) with a β-aminoaldehyde of formula (III):

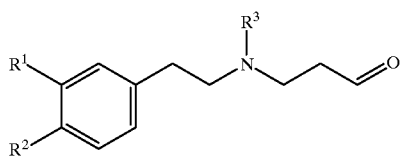

wherein $R^1$, $R^2$ and $R^3$ are as defined in relation to formula (I); and thereafter reducing the intermediate so formed and, optionally, forming an addition salt of the compound of formula (I) and/or a solvate thereof.

2. A process according to claim 2, wherein the intermediate is an imine of formula (V):

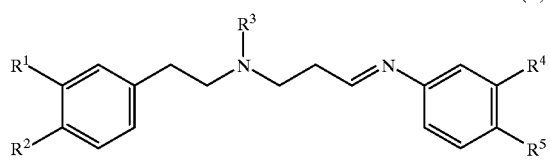

wherein $R^1$, $R^2$, $R^4$ and $R^5$ are each independently $C_{1-4}$ alkoxy and $R^3$ is $C_{1-6}$ alkyl.

3. A process according to claim 2, wherein $R^1$, $R^2$, $R^4$ and $R^5$ each independently represent methoxy.

4. A process according to claim 2, wherein $R^3$ represents methyl.

5. A process according to claim 1, for the preparation of N-[2-(3,4-Dimethoxyphenyl)ethyl]-N-methyl-N'-(3,4-dimethoxyphenyl)-1,3-propanediamine, hydrochloride.

6. A compound of formula (III):

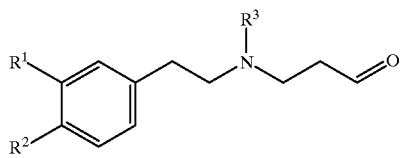

wherein $R^1$ and $R^2$ are each independently $C_{1-4}$ alkoxy and $R^3$ is $C_{1-6}$ alkyl.

7. A compound of formula (V):

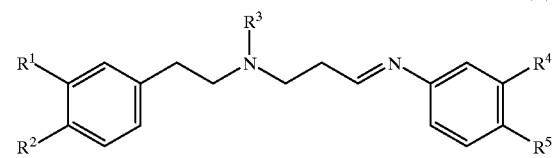

wherein $R^1$, $R^2$, $R^4$ and $R^5$ are each independently $C_{1-4}$ alkoxy and $R^3$ is $C_{1-6}$ alkyl.

* * * * *